(12) United States Patent
de Oliveira et al.

(10) Patent No.: US 9,052,588 B2
(45) Date of Patent: Jun. 9, 2015

(54) COMPOSITION FOR PRODUCING OPTICAL ELEMENTS HAVING GRADIENT STRUCTURE

(75) Inventors: Peter William de Oliveira, Saarbruecken (DE); Peter Koenig, Lebach (DE); Michael Veith, St.-Ingbert (DE); Omid Yazdani-Assl, Saarbruecken (DE)

(73) Assignee: Leibniz-Institut fuer Neue Marterialien gemeinnuetzige GmbH, Saarbruecken (DE)

( * ) Notice: Subject to any disclaimer, the term of this patent is extended or adjusted under 35 U.S.C. 154(b) by 0 days.

(21) Appl. No.: 13/124,850

(22) PCT Filed: Oct. 16, 2009

(86) PCT No.: PCT/EP2009/007458
§ 371 (c)(1),
(2), (4) Date: Apr. 19, 2011

(87) PCT Pub. No.: WO2010/046066
PCT Pub. Date: Apr. 29, 2010

(65) Prior Publication Data
US 2011/0236804 A1    Sep. 29, 2011

(30) Foreign Application Priority Data
Oct. 21, 2008 (DE) .......................... 10 2008 052 586

(51) Int. Cl.
*G03H 1/02* (2006.01)
*G03F 7/00* (2006.01)
(Continued)

(52) U.S. Cl.
CPC . *G03F 7/001* (2013.01); *C08K 5/56* (2013.01); *G03H 1/00* (2013.01); *B29C 71/04* (2013.01);
(Continued)

(58) Field of Classification Search
CPC ............. C08K 5/56; G03F 7/00; G03F 7/004; G03H 1/00; B29C 71/04; B29D 11/00355; C07C 31/28; C07F 11/00; C07F 13/00; C07F 15/00; C07F 17/00; C07F 19/00; C07F 7/00; C07F 7/28; C07F 9/00; C08J 3/20; G02B 5/00; G02B 5/18; G02B 6/00; G02B 5/32
See application file for complete search history.

(56) References Cited

U.S. PATENT DOCUMENTS 3,098,863 A * 7/1963 Dessauer et al. .............. 556/150
3,485,765 A * 12/1969 Newland ....................... 252/586
(Continued)

FOREIGN PATENT DOCUMENTS

DE    102004061323 A1    6/2006
DE    102006011949 A1    9/2007
(Continued)

OTHER PUBLICATIONS

Translation of JP-2007-298841(Nov. 2007).*
(Continued)

*Primary Examiner* — Martin Angebranndt
(74) *Attorney, Agent, or Firm* — Cahn & Samuels, LLP

(57) ABSTRACT

A composition for producing optical elements has a gradient structure, particularly for holographic applications, wherein the gradient structure is formed by a refractivity gradient. The composition is produced from a polymer and a light- and/or temperature-sensitive metal complex and the light- and/or temperature-sensitive metal complex is decomposed upon changing the local refractivity. The result is the formation of a refractivity gradient.

13 Claims, 6 Drawing Sheets

(51) Int. Cl.

| | |
|---|---|
| *C08K 5/56* | (2006.01) |
| *G03H 1/00* | (2006.01) |
| *B29C 71/04* | (2006.01) |
| *B29D 11/00* | (2006.01) |
| *C07C 31/28* | (2006.01) |
| *C07F 11/00* | (2006.01) |
| *C07F 13/00* | (2006.01) |
| *C07F 15/00* | (2006.01) |
| *C07F 17/00* | (2006.01) |
| *C07F 19/00* | (2006.01) |
| *G02B 5/18* | (2006.01) |
| *C07C 45/77* | (2006.01) |
| *G02B 5/32* | (2006.01) |
| *G03F 7/004* | (2006.01) |

(52) U.S. Cl.
CPC .......... *B29D 11/00355* (2013.01); *C07C 31/28* (2013.01); *C07F 11/00* (2013.01); *C07F 13/00* (2013.01); *C07F 15/00* (2013.01); *C07F 17/00* (2013.01); *C07F 19/00* (2013.01); *G02B 5/18* (2013.01); *C07C 45/77* (2013.01); *G02B 5/32* (2013.01); *G03F 7/0043* (2013.01)

(56) References Cited

U.S. PATENT DOCUMENTS

| | | | | |
|---|---|---|---|---|
| 3,494,896 | A | * | 2/1970 | Aoki et al. ............. 528/55 |
| 3,512,975 | A | * | 5/1970 | Hackmann et al. ..... 430/292 |
| 3,554,996 | A | * | 1/1971 | Beck ................... 524/87 |
| 3,558,519 | A | * | 1/1971 | Phung et al. ......... 502/117 |
| 3,565,929 | A | * | 2/1971 | Seki et al. ............ 556/88 |
| 3,647,746 | A | * | 3/1972 | Seki et al. ........... 524/182 |
| 3,717,558 | A | * | 2/1973 | McGinniss ............ 522/27 |
| 3,772,354 | A | * | 11/1973 | Fredricks et al. ...... 556/45 |
| 4,042,764 | A | * | 8/1977 | Gratani et al. ........ 523/126 |
| 4,256,627 | A | * | 3/1981 | Moser et al. .......... 524/100 |
| 4,328,303 | A | * | 5/1982 | Ronn et al. ........... 430/290 |
| 4,403,031 | A | * | 9/1983 | Borrelli et al. ........ 430/332 |
| 4,694,138 | A | * | 9/1987 | Oodaira et al. ........ 219/121.85 |
| 4,808,640 | A | * | 2/1989 | Morita et al. .......... 523/433 |
| 4,959,207 | A | * | 9/1990 | Ueda et al. ........... 424/76.1 |
| 4,978,604 | A | * | 12/1990 | Banks et al. ........... 430/327 |
| 5,332,794 | A | * | 7/1994 | Ohtsu et al. ........... 526/169.1 |
| 5,529,473 | A | | 6/1996 | Lawton et al. |
| 5,552,261 | A | | 9/1996 | Kraska et al. |
| 5,942,376 | A | | 8/1999 | Uchida et al. |
| 6,048,660 | A | * | 4/2000 | Leppard et al. ........ 430/270.1 |
| 6,567,204 | B1 | * | 5/2003 | Wang et al. ........... 359/265 |
| 7,138,219 | B2 | * | 11/2006 | Kuroki ................. 430/281.1 |
| 8,133,940 | B2 | * | 3/2012 | Zalich et al. .......... 523/300 |
| 2003/0190820 | A1 | | 10/2003 | Hill et al. |
| 2004/0034245 | A1 | | 2/2004 | Okamura et al. |
| 2005/0101698 | A1 | | 5/2005 | Harada et al. |
| 2006/0090596 | A1 | * | 5/2006 | Goia et al. ............ 75/371 |
| 2006/0216437 | A1 | | 9/2006 | Murakami ............. 428/1.3 |
| 2007/0194288 | A1 | * | 8/2007 | Lee et al. .............. 252/500 |
| 2008/0247009 | A1 | * | 10/2008 | Mennig et al. ........ 359/3 |
| 2009/0091833 | A1 | | 4/2009 | Mennig et al. |
| 2009/0288517 | A1 | * | 11/2009 | Chretien et al. ....... 75/371 |

FOREIGN PATENT DOCUMENTS

| | | | |
|---|---|---|---|
| GB | 734113 A | | 7/1955 |
| GB | 1169011 A | | 10/1969 |
| JP | 63-128038 | * | 5/1988 |
| JP | 05-132507 | * | 5/1993 |
| JP | 2007-070722 | * | 3/2007 |
| JP | 2007298841 A | | 11/2007 |
| WO | 2004077530 A2 | | 9/2004 |
| WO | WO2004077530 A2 | | 9/2004 |
| WO | 2006/067061 | * | 6/2006 |

OTHER PUBLICATIONS

Kometani et al. "Preparation of colloidal silver nanoparticles using benzoin as a photoinitiator" Coll Surf., A, Physicochem Eng Asp., vol. 313-314 pp. 43-46 (May 2007).*

Itakura et al. "Preparation and characterization of ultrafine metal particles in ethanol by UV irradiation using a photoinitiator"., Langm., vol. 11(10) pp. 4129-4134 (1995).*

Ott, Timo, "Synthesis and application of highly functionalized acylphosphane oxides", Thesis (331 pages) (Jan. 2008).*

McGilvray et al., "Facile photochemical synthesis of unprotected aqueous gold nanoparticles", JACS Commun., vol. 128(50) pp. 15980-15981 (2006).*

Smirnova et al., "UV induced formation of gold nanoparticles in poly(methyl methacrylate) matrix" Dok. Phys. Chem., vol. 400(2) pp. 19-21 (2005).*

Cardone et al., "Polymeric nanocomposite based on gold particles", AIP Conf. Pric., vol. 1042 pp. 231-233 (Aug. 2008).*

Kapoor et al., "Photochemical formation of copper nanoparticles in poly(N-vinylpyrrolidone)" Chem. Phys. Let., vol. 370 pp. 83-87 (2003).*

Mendoza et al. "Photolithography of integrated optic devices in sol-gel glasses", Proc. SPIE vol. 2288 pp. 580-588 (1994).*

Wojcik et al. "Transparent poly(vinyl acetate)-silica gels by a sol-gel process", Proc. SPIE vol. 2018 pp. 160-166 (1993).*

Yoshida et al. "Sol-gel based polyvinylpyrrolidone/silicon oxide composite and novel fabrication technique for channel waveguide" Mat. Res. Soc. Symp. Proc., vol. 392 pp. 103-108 (1995).*

Luckemeyer et al. "Profiles in volume phase holograms in CP2TiCl2:PMMA", Appl.Phys. B vol. 46 pp. 157-164 (1988).*

Martoz, "Holographic storage in sensitized polymethyl methacrylate blocks", Appl. Phys. B., vol. 37 pp. 181-187 (1985).*

English abstract of WO2004077530 (A2).

English abstract of JP2007298841 (A).

English Translation of International Preliminary Report on Patentability for PCT Application No. PCT/EP2009/007458.

* cited by examiner

COMPOSITION FOR PRODUCING OPTICAL ELEMENTS HAVING GRADIENT STRUCTURE

This patent application is a U.S. national stage application of PCT international application PCT/EP2009/007458 filed on 16 October 2009 and claims priority of German patent document 10 2008 052 586.3 filed on 21 Sep. 2008.

FIELD OF THE INVENTION

The invention relates to a composition for producing optical elements with gradient structure, especially for holographic applications, wherein the gradient structure is formed by a refractive index gradient, and to a process for producing these optical elements with gradient structure.

BACKGROUND OF THE INVENTION

U.S. Pat. Nos. 5,552,261 and 5,529,473 disclose using the diffusion of monomers which have an increased or decreased refractive index compared to a surrounding liquid matrix for generation of a refractive index gradient. This effect, which is known as the Colburn-Haines effect for polymers, can lead after subsequent polymerization to a product with refractive index gradients. Such polymers are also referred to as photopolymers. To produce the refractive index gradient, a local polymerization is induced, which leads to a potential difference. This promotes the diffusion of further monomers to the site of local polymerization. This alters the refractive index at this point compared to the direct environment.

The generation of sharp refractive index gradients by the Colburn-Haines effect therefore requires not only the efficient diffusion of the monomers but also rapid and efficient depletion of the monomers. The matrix is usually a polymer which, for example, is dissolved in a solvent. It is important that the reaction of the monomers must not influence the matrix. Moreover, the formation of the refractive index gradient should not lead to a change in the overall material, for example as the result of shrinkage. This is important especially in the generation of refractive index gradients in very thick layers.

One problem in the generation of refractive index gradients on the basis of purely organic systems is the limited range of refractive indices achievable. One means of increasing the range is the use of inorganic components.

For example, in application US 2005/0101698, a concentration gradient of nanoparticles is generated in a composite material. This process allows the production of volume holograms with a refraction efficiency of 90%. However, the thickness of the layers is limited and the material exhibits high shrinkage due to the free-radical polymerization. Moreover, the slow diffusion of the nanoparticles limits the possible refractive indices and useable matrices.

In summary, it can be stated that the development of photopolymers has recorded great advances in the last few years. Nevertheless, the known systems still have some disadvantages. For instance, the systems used are not sensitive enough to enable very sharp modulation of the refractive index. The sensitivity includes the light intensity required for polymerization, and also the exposure time required for production of the gradient structure. Both limit resolution and refraction efficiency in the gradient structures produced. At the same time, the range of refractive index modulation achieved in the material also plays an important role. Both parameters mentioned, for example, limit the minimum layer thickness of the material with which the production of optical gradient structures is still possible.

Since optical gradient structures are nowadays used in many fields with very different requirements, for example with regard to mechanical flexibility, thickness and stability, high variability of the components used is of great significance.

It is an object of the invention to provide a simple, universally applicable and inexpensive process for producing optical elements with gradient structure, which overcomes the stated disadvantages of the prior art.

SUMMARY OF INVENTION

This object is achieved by the inventions with the features of the independent claims. Advantageous developments of the inventions are characterized in the dependent claims. The wording of all claims is hereby incorporated into this description by reference. The invention also encompasses all viable and more particularly all mentioned combinations of independent and/or dependent claims.

The object is surprisingly achieved by a composition which comprises at least one organic or inorganic polymer and at least one mono- or polynuclear metal complex which contains at least one light-sensitive and/or thermally sensitive group.

Advantageously, the composition comprises more than 5% by weight, preferably 5 to 90% by weight, more preferably 30 to 90% by weight, of the mono- or polynuclear metal complex.

The composition may additionally comprise one or more solvents. Suitable solvents are all solvents in which the organic or inorganic polymer and the mono- or polynuclear metal complex dissolve. The proportion of solvent can be adjusted to the requirements and may be between 0 and 60% by weight. Preference is given to organic solvents. It is also possible to use mixtures. Examples of organic solvents are ketones such as acetone, esters such as ethyl acetate, ethers such as diethyl ether or tetrahydrofuran, glycols such as ethylene glycol, aliphatic, aromatic or halogenated hydrocarbons, such as hexane, benzene, dichloromethane or chloroform.

In addition, a low level, up to 5% by weight, of customary additives, such as wetting aids, adhesion promoters, leveling agents, antioxidants, stabilizers, dyes, photochromic or thermochromic compounds or plasticizers, may be present.

Without being bound to a particular theory, it is assumed that the metal complex decomposes in accordance with its light-sensitive and/or thermally sensitive groups and in this way leads to local formation of inorganic components in the composition. This generates a potential difference which promotes the diffusion of further metal complexes to this point, which are likewise decomposed. This results in an alteration in the local refractive index at the site of decomposition and to the formation of a refractive index gradient.

In an advantageous development, the metal complex comprises a metal of groups 4 to 12, preferably Ti, Zr, Ta, V, Nb, Cr, Mo, W, Mn or Re, more preferably Ti, Ta or Zr.

Light-sensitive and/or thermally sensitive groups are understood in the context of the invention to mean groups which decompose under the action of light and/or heat. More particularly, this means the cleavage of covalent bonds. This does not involve polymerization or polycondensation of these groups. It is only the decomposition of these groups that destabilizes the complex.

In addition to the light-sensitive and/or thermally sensitive groups, the complex may contain further groups which stabilize the complex, for example alkoxides, 1,3-diketones, amines, amides or cyclopentadienes.

In an advantageous development, the mono- or polynuclear metal complex comprises exclusively light-sensitive and/or thermally sensitive groups.

Possible thermally sensitive groups are organic peroxides, in the form of diacyl peroxides, peroxydicarbonates, alkyl peresters, dialkyl peroxides, perketals, ketone peroxides and alkyl hydroperoxides.

Possible light-sensitive groups are, for example, alkyl benzoylformates, amino ketones, benzoin ethers, benzophenones, dimethyl ketals, glyoxylates, hydroxy ketones, hydroxyphenones, metallocenes, organic iodine compounds, phenyl ketones, phenylpropanes and phosphine oxides; preference is given to groups which can conduct Norrish type I reactions. These are, for example, customary photoinitiators for polymerizations, such as α-hydroxy ketones, glyoxylates or amino ketones. Examples of commercially groups are photoinitiators of the Irgacure® or Darocur® type, such as Irgacure 184 (1-hydroxycyclohexyl phenyl ketone), Irgacure 2959 (2-hydroxy-1-[4-(2-hydroxyethoxy)phenyl]-2-methyl-1-propanone), Irgacure 754, Irgacure 651 (α,α-dimethoxy-α-phenylacetophenone), Irgacure 819, Darocur 1173 (2-hydroxy-2-methyl-1-phenyl-1-propanone), Darocur MBF (methyl benzoylformate), Darocur 4265, Darocur TPO. It is also possible to use derivatives of these photoinitiators, for example derivatives which enable attachment to the metal site, for example by means of additionally introduced groups such as hydroxyl groups, $C_{1-2}$-alkoxy groups, carbonic acid groups or amines.

In an advantageous development, the reactive region of the light-sensitive group is bonded to the metal of the metal complex via not more than three bonds. The reactive region of the group is the region of the structure which is crucial in the reaction of the group with light. In the case of α-hydroxy ketones, this would be the combination of the hydroxyl group and of the keto group adjacent thereto. Preference is given to very direct proximity between the metal site and the reactive region of the group, for example by the direct bond via the α-hydroxyl group of the α-hydroxy ketones, for example of Irgacure 184 or Darocur 1173. Such compounds can be obtained, for example, by conversion of the corresponding metal chlorides or metal alkoxides.

The polymer of the composition may be an organic or inorganic polymer. It is preferably soluble in the composition. The polymer preferably takes no part in the formation of the refractive index gradient but serves as a matrix for the refractive index gradient which forms. However, the polymer content in the composition can influence the formation of the refractive index gradient, for example by influencing the diffusion. Moreover, the polymer, after the production of the refractive index gradient, serves to stabilize this gradient.

The proportion of polymer may be between 1 and 99% by weight. Preference is given to a content of 30 to 80% by weight.

In an advantageous development, the polymer does not have any reactive groups which can polymerize or polycondense as a result of the decomposition of the metal complex.

Preference is given to a polymer with a mean molecular weight of more than 50 000 daltons, preferably more than 150 000 daltons.

The polymer may be a polymerized or polycondensed organic oligomer and/or prepolymer, an organic polymer and/or a condensate formed from one or more hydrolysable, optionally organically modified inorganic compounds. Preference is given to an organic polymer.

The organic polymers may be any desired known polymers. Preference is given to polymers which dissolve in the abovementioned solvents or mixtures thereof, for example polyacrylic acid, polymethacrylic acid and derivatives, polyacrylates, polymethacrylates, polyethylene glycols, polyolefins, polystyrene and polystyrene derivatives, polyamides, polyimides, polyvinyl compounds such as polyvinyl chloride, polyvinyl alcohol, polyvinyl butyral, polyvinyl acetate, polyvinylpyrrolidone, paravinylguaiacol, and corresponding copolymers, for example poly(ethylene-vinyl acetate), polyesters, e.g. polyethylene terephthalate or polydiallyl phthalate, polyarylates, polycarbonates, polyethers, e.g. polyoxymethylene, polyethylene oxide and polyphenylene oxide, polyether ketones, polysulfones, polyepoxides, fluoropolymers, e.g. polytetrafluoroethylene, and organopolysiloxanes. The polymers are preferably transparent polymers. Preference is given to poly(meth)acrylic acid and derivatives, poly(meth)acrylates, poly(meth)acrylonitriles, polystyrenes or polystyrene derivatives, polyalkenes, halogenated polyalkenes, polyvinyl acetate, polyvinylpyrrolidone, polyvinylcarbazole, poly(polyethylene glycol)(meth)acrylates, poly(polyethylene glycol)di(meth)acrylates.

The composition can be used as a coating or as a molding material. The solvent content in the course of application may differ from the content during the treatment to generate the refractive index gradient.

The composition may also comprise sensitizers, for example benzophenones, in order, for example, to achieve sensitivity of the composition for a particular wavelength. The proportion of these sensitizers may be 0 to 15% by weight.

The composition may also comprise further components, for example high or low refractive index nanoparticles, for example of metal oxides, which may also be surface-modified.

The composition may also comprise a further curable inorganic or organic matrix material. After the establishment of the refractive index gradient, this matrix material can be cured for further stabilization of the gradient. This material is advantageously inert with respect to the reactions which lead to the establishment of the refractive index gradient.

The invention further relates to a metal complex, especially for photolytic decomposition to obtain refractive index gradients. Advantageously, the complex has the formula $$X_{(m-n)}MR^1_n \qquad (I)$$

where M is a metal or semimetal of groups 2 to 16 of the Periodic Table, preferably a metal of groups 4 to 12, more preferably Ti, Zr, Ta, V, Nb, Cr, Mo, W, Mn or Re.

$R^1$ is a light-sensitive group and X is a group without a light-sensitive group. The value of m is greater than n and m corresponds to the valency of the metal. n is at least 1 and preferably equal to m.

In a preferred development, the reactive region of the light-sensitive group, which is as defined above, is bonded to M via not more than three bonds. This means that, for example, in a structural formula of the complex according to the customary valence notation, there are not more than three bonds between the reactive region and the metal complex. The reactive region is all bonds directly involved in the photochemical reaction of the light-sensitive group, for example at least the cleaved bond in the case of a Norrish type I reaction.

$R^1$ may, for example, be selected from the group comprising alkyl benzoylformates, amino ketones, benzoin ethers, benzophenones, dimethyl ketals, glyoxylates, hydroxy ketones, hydroxyphenones, metallocenes, organic iodine compounds, phenyl ketones, phenylpropanes and phosphine oxides. As mentioned above, these groups may be bonded to M via a short linker, for example via a heteroatom, preferably N or O, and via a short alkylene bridge, where the bridge may also be interrupted by heteroatoms. Preference is given to compounds which can conduct Norrish type I reactions.

$R^1$ may also be derived from customary photoinitiators for polymerizations, such as α-hydroxy ketones, glyoxylates or amino ketones, for example from photoinitiators of the Irgacure® or Darocur® type, such as Irgacure 184 (1-hydroxy-cyclohexyl phenyl ketone), Irgacure 2959 (2-hydroxy-1-[4-(2-hydroxyethoxy)phenyl]-2-methyl-1-propanone), Irgacure 754, Irgacure 651 (α,α-dimethoxy-α-phenylacetophenone), Irgacure 819, Darocur 1173 (2-hydroxy-2-methyl-1-phenyl-1-propanone), Darocur MBF (methyl benzoylformate), Darocur 4265, Darocur TPO. These structures may be bonded to M via the heteroatoms present or via those introduced, or short alkoxy bridges. Preference is given to attachment via heteroatoms of the reactive region of the photoinitiators, for example via the α-hydroxyl group of the α-hydroxy ketones. The metal complex preferably contains only one kind of ligand.

X is a group which does not contain a light-sensitive group. Preference is given to alkoxides, 1,3-diketones, amines which may also be alkylated, amides or cyclopentadienes. Also possible are polydentate ligands which may likewise contain heteroatoms.

It is preferably a metal complex of the formula

$$M\text{-}(-Z-CR^2R^3-CO-R^4)_m \quad (II)$$

where M is as defined above. Z is a heteroatom, preferably O, N or S, where Z in the case of N may also be alkylated, preferably methylated.

$R^2$ and $R^3$ are the same or different, preferably a $C_1$-$C_{12}$ alkyl radical or an aryl radical, more preferably methyl or ethyl, propyl, isopropyl or phenyl, where the radicals may also be substituted. $R^2$ and $R^3$ may also be joined to one another via an alkylene bridge, preferably a $C_6$-alkylene bridge, which may likewise be interrupted by heteroatoms.

$R^4$ is a $C_1$-$C_6$ alkyl group, or an aryl group which is unsubstituted or substituted by $C_1$ to $C_3$ alkyl radicals, where the groups may also contain heteroatoms or halogens. $R^4$ is preferably an unsubstituted or substituted phenyl group, where the group may be substituted by halogens, or methyl or ethyl groups. $R^4$ is preferably a phenyl group.

M corresponds to the valency of the metal.

Examples of such complexes are $Ti(OC_3H_6COC_6H_5)_4$, $Zr(OC_3H_6COC_6H_5)_4$ or $Ta(OC_3H_6COC_6H_5)_4$.

In addition, the invention also relates to a process for producing an optical element.

Individual process steps are described in detail hereinafter. The steps need not necessarily be conducted in the sequence specified, and the process to be outlined may also have further unspecified steps.

In a first step, a composition composed of at least one organic or inorganic polymer and at least one mono- or polynuclear metal complex which at least one light-sensitive and/or thermally sensitive group, and at least one solvent is produced.

Advantageously, the inventive composition is used. The metal complex used is preferably an inventive metal complex.

Advantageously, the composition is present as a solution or emulsion.

The components for production of the composition or a precursor thereof can be mixed with one another in any desired manner and sequence.

It is also possible to add further additives, for example wetting aids, adhesion promoters, leveling agents, antioxidants, stabilizers, dyes, photochromic or thermochromic compounds or plasticizers, but only up to 5% by weight.

The composition can be used as a coating composition or as a molding material. Depending on this, the viscosity can be adjusted, for example, by the amount of solvent or by the type of polymer used. For instance, the composition is applied to a surface or introduced into a mold.

The further treatment can optionally be preceded by a reduction in the solvent content, for example by drying.

In the next step, a potential difference is generated in the composition for directed diffusion of the metal complexes through local decomposition of the metal complexes.

The potential difference preferably generates a chemical potential difference, for example analogously to the above-described Colburn-Haines effect. In the case of a local (for example thermally and/or photochemically induced) decomposition of the metal complex, this leads to a reduction in the concentration of the metal complex in these regions. This leads to directed diffusion of undecomposed metal complexes into the (heated or exposed) regions, in order to balance out the chemical potential difference. These metal complexes are available for decomposition in these regions. In the heated or exposed regions, this leads to a change in the optical density and hence to a local increase or reduction in the refractive index.

Decomposition is understood to mean the conversion of the metal complex with alteration of the refractive index. The complex preferably decomposes with elimination of the light-sensitive and/or thermally sensitive ligands. Without being bound to a theory, this forms inorganic compounds, for example metal oxides, which influence the local refractive index. This preferably does not involve any polymerization or polycondensation reaction of the ligands, as, for example, in the formation of polymers. Nor do the ligands act as polymerization initiators. The composition therefore preferably does not comprise any monomers for polymers, not even as ligands, for example methacrylates or epoxides. The change in the refractive index proceeds from the inorganic component of the complex formed in the decomposition.

The chemical potential difference is preferably generated by exposure or electron irradiation, especially by holographic or lithographic techniques, or by means of the mask aligner technique. By selective irradiation or exposure of the composition, it is possible, for example at local sites, to trigger controlled decomposition of the metal complex, which leads to a chemical potential difference, which in turn leads to the directed diffusion of the metal complexes and to the formation of a refractive index gradient.

Without being bound to a particular system, one possible explanation would be that the local decomposition forms a component with a particular refractive index, or the concentration thereof is increased there, which is balanced by the fact that the refractive index of the other regions is likewise altered by the diffusion of the metal complexes.

It follows from this that, as mentioned above, the change in the refractive index should always be considered in relation to the adjacent regions. What is crucial is the resulting difference in the refractive index. Which region has a higher or lower refractive index can be determined, for example, by the selection of the polymer or of the metal complexes, or of the metal, or of other components.

For the exposure processes, preference is given to using UV light or laser light. In the case of use of a laser as the light source, it is possible by means of holographic techniques to produce either periodic grid structures or Fresnel structures.

The intensity profiles which occur as a result of interference act as polymerization sinks. For the particularly preferred holographic exposure, it is possible to produce, for example by means of two-wave mixing, phase-modulated volume holograms as transmission or reflection holograms.

The coherent light source used may, for example, be an argon ion laser.

After the production of the gradient structure, the undecomposed metal complexes can be depleted homogeneously by a non-local decomposition, for example a non-intensity-modulated exposure. Since no further directed diffusion at all occurs in this case, there is no more than attenuation of the refractive index gradient already generated. However, this can distinctly improve the lifetime of the gradient structures produced.

In addition, the invention relates to an optical element obtainable from an inventive composition.

The inventive optical element or the compositions are especially suitable for production of optical elements with a refractive index gradient. The optical elements are especially suitable as holographic applications, light management films, diffusers, planar gradient index lenses in imaging optics, head-up displays, head-down displays, light waveguides, in particular in optical telecommunications and transmission technology, and optical data stores. Examples of producible optical elements are security holograms, picture holograms, digital holograms for information storage, systems comprising components which process light wavefronts, planar waveguides, beam splitters and lenses.

The invention further relates to the use of the inventive metal complex for production of optical elements.

The invention also relates to the use of inventive optical elements for holographic applications, planar gradient index lenses in imaging optics, light management films, diffusers, head-up displays, head-down displays, light waveguides and optical data stores.

Further details and features are evident from the following description of preferred working examples, in conjunction with the dependent claims. In this context, the particular features can each be implemented alone, or several in combination with one another. The means of achieving the object are not restricted to the working examples. For example, stated ranges always include all unspecified intermediate values and all conceivable partial ranges.

First, a composition is produced from the metal complex and the polymer. In order to obtain a homogeneous composition, preference is given to preparing a solution. The components can be mixed in different sequence. This mixture preferably comprises a proportion of 5 to 60% by weight of metal complex, 5 to 50% by weight of polymer and 20 to 80% by weight of one or more solvents.

For the coating, preference is given to selecting suitable substrates for optical applications, for example glass, ceramic, silicon, metal, semiconductor materials or (preferably transparent) polymers, such as PET, PE and PP. A particularly preferred substrate is a polymer film. The coating can be effected by customary methods, for example by dipping, flow coating, knife coating, pouring, spin coating, spraying, brushing, slot coating, meniscus coating, film casting or spinning. Suitable for this purpose are naturally liquid precursors of the composition, in which case the viscosity required can be established, for example, by adding or removing solvent(s). Alternatively, the selection of the polymer can influence the viscosity. Preferred layer thicknesses (of the finished coating) are 0.2 to 300 µm, more preferably between 0.2 and 100 µm.

In this form, the film material can be stored in wound, light-protected and climatized (15 to 30° C.) form. In this way, a film assembly or composite can also be produced. Films with a coating which has a refractive index gradient, onto which a second film has optionally been laminated (film composite), are preferred inventive optical elements.

Subsequently, a potential difference is generated in the composition in the manner described above, such that directed diffusion and induced local decomposition of the metal complex form a refractive index gradient. The potential difference is preferably generated by an exposure process.

In a preferred embodiment of the invention for producing a transmission hologram, such an inventive composition is applied to a glass surface and dried. This produced layers with a thickness between 8 and 200 µm. With the aid of two-wave mixing of a laser beam with a wavelength between 300 nm and 500 nm and an intensity between 7 and 300 mW/cm$^2$, phase-modulated volume holograms are generated either in the form of transmission holograms or in the form of reflection holograms. The exposure time is between 1 second and 10 minutes, preferably between 1 and 3 minutes.

The processes which occur in generation of a potential difference are explained below for a preferred embodiment.

Local exposure locally decomposes the metal complexes to change the local refractive index. This forms a chemical potential gradient for as yet undecomposed metal complexes to the unexposed neighboring region. From this neighboring region, further metal complexes therefore diffuse into the exposed region. This process can proceed during and after the exposure, and lasts for between a few seconds and a few minutes, according to the exposure conditions and temperature. As a result of the difference in refractive index between the different regions with different decomposition, a local refractive index gradient arises in this way.

In summary, the process according to the invention allows, in an inexpensive and efficient manner, the production of gradient structures which comprise inorganic components, without having to sacrifice the rapid diffusion of the active components. This can achieve, for example, with the same thickness of the material, a significant improvement in the optical properties. In this way, the production of such systems becomes much simpler and less expensive. At the same time, great variability can also be achieved, for example with regard to the metal complexes and polymers used, since the properties of the metal complexes and/or of the polymer can be adjusted very flexibly to the desired conditions.

DETAILED DESCRIPTION OF INVENTION

Figure 1:
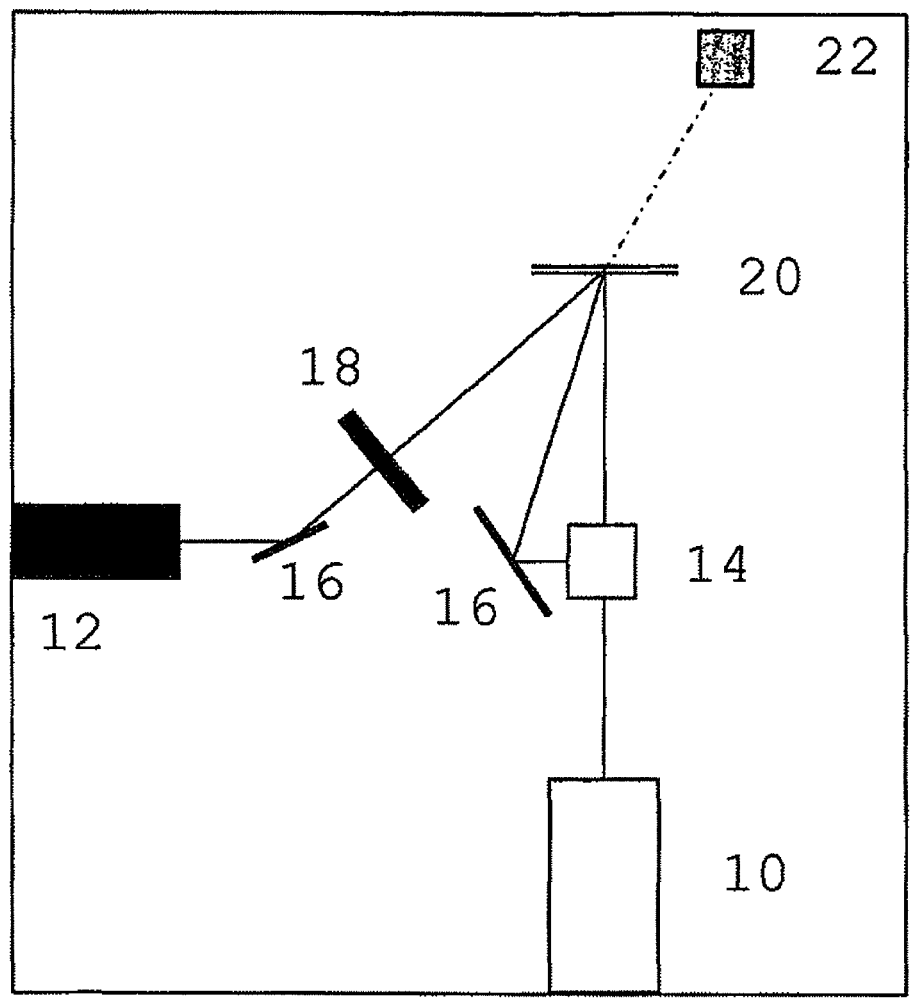
FIG. 1 experimental structure for generation and analysis of the holograms

FIG. 1 shows the structure used to generate the holograms. An Ar$^+$ ion laser (10) was used for writing. The writing process can be controlled by an He laser (12). The hologram itself was generated by means of a beam splitter (14) in the beam path of the Ar+ ion laser (10). These beams and the beam of the He laser (12) via several mirrors (16) to the sample (20) passed. To detect the hologram with the aid of the He laser (12), a chopper (18) and a detector connected to a lock-in amplifier (22) were used.

Figure 2:
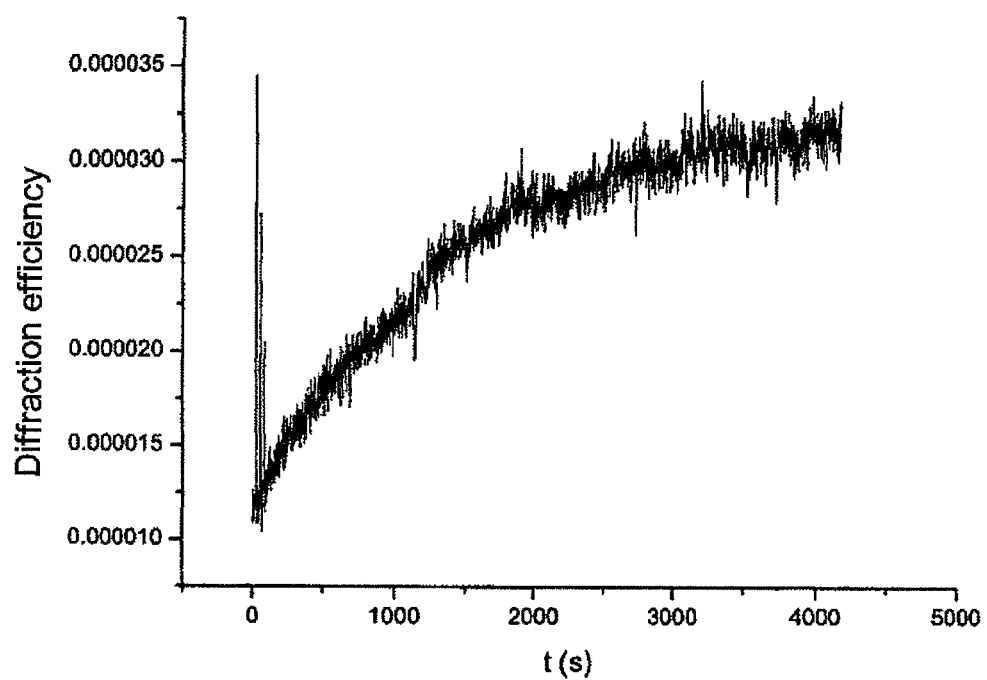
FIG. 2 plot of the diffraction efficiency at the first diffraction maximum from example 1.
Figure 3:
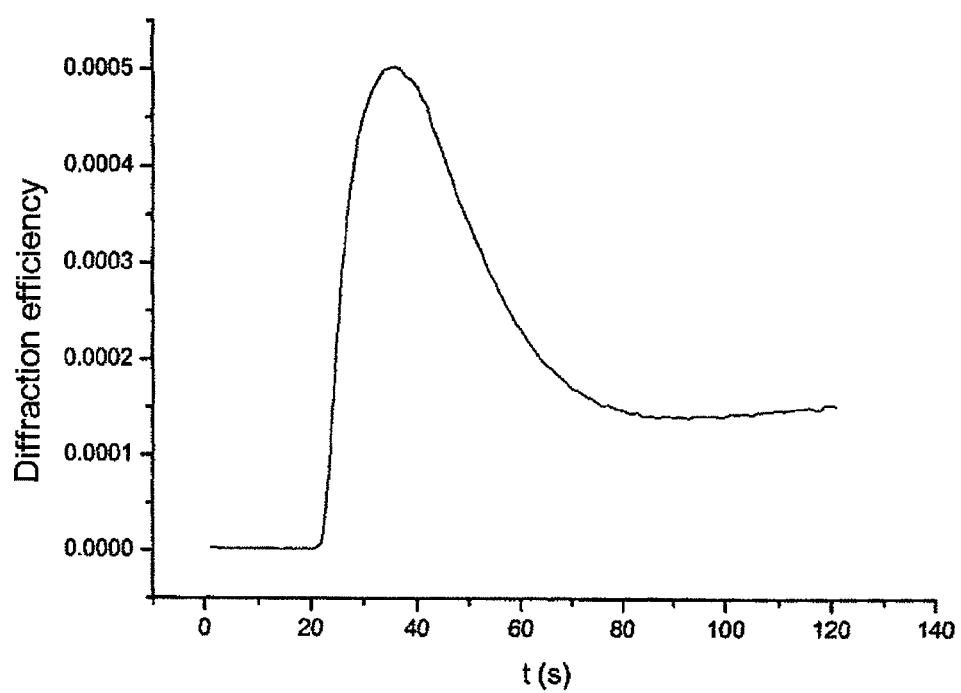
FIG. 3 plot of the diffraction efficiency at the first diffraction maximum from example 2.

FIG. 2 shows the plot of the diffraction efficiency at the first diffraction maximum after three times briefly irradiating a composition from example 1;

FIG. 3 shows the plot of the diffraction efficiency at the first diffraction maximum from example 2. During the exposure, the sample was not covered with a glass plate.

Figure 4:
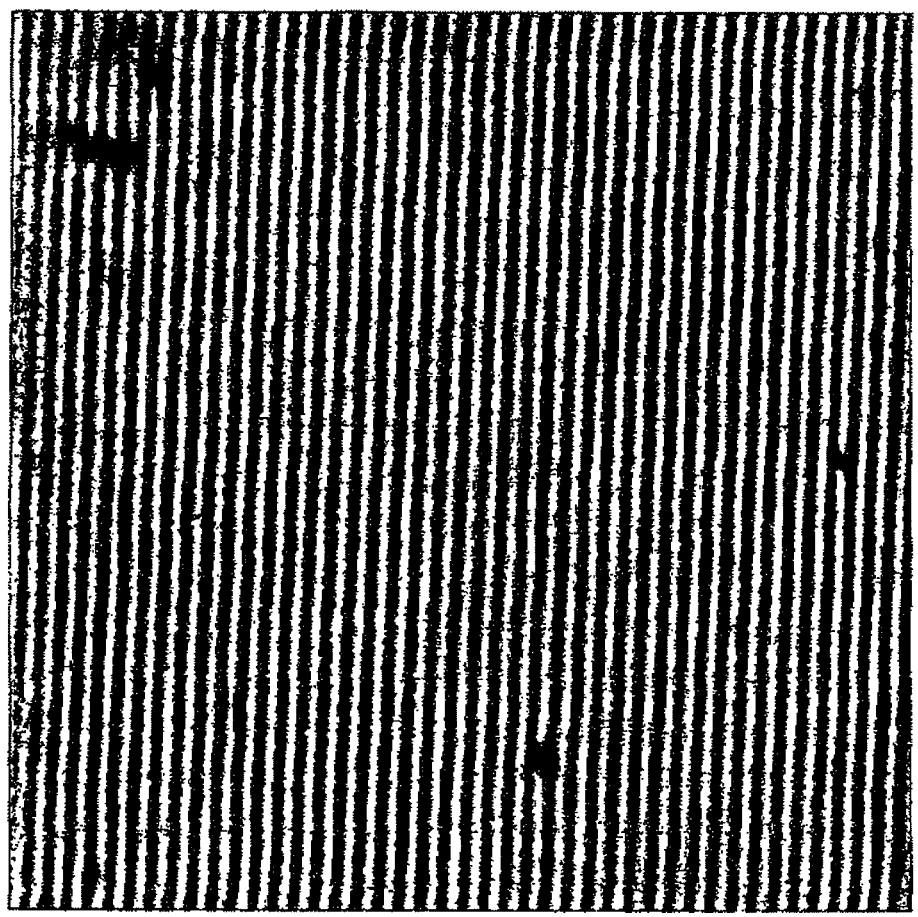
FIG. 4 light microscopy image of the hologram from example 2.

FIG. 4 shows the hologram obtained from example 2 under a light microscope. The distance between the lines from middle to middle is ~10 µm; the width of the lines is about 2 µm.

Figure 5:
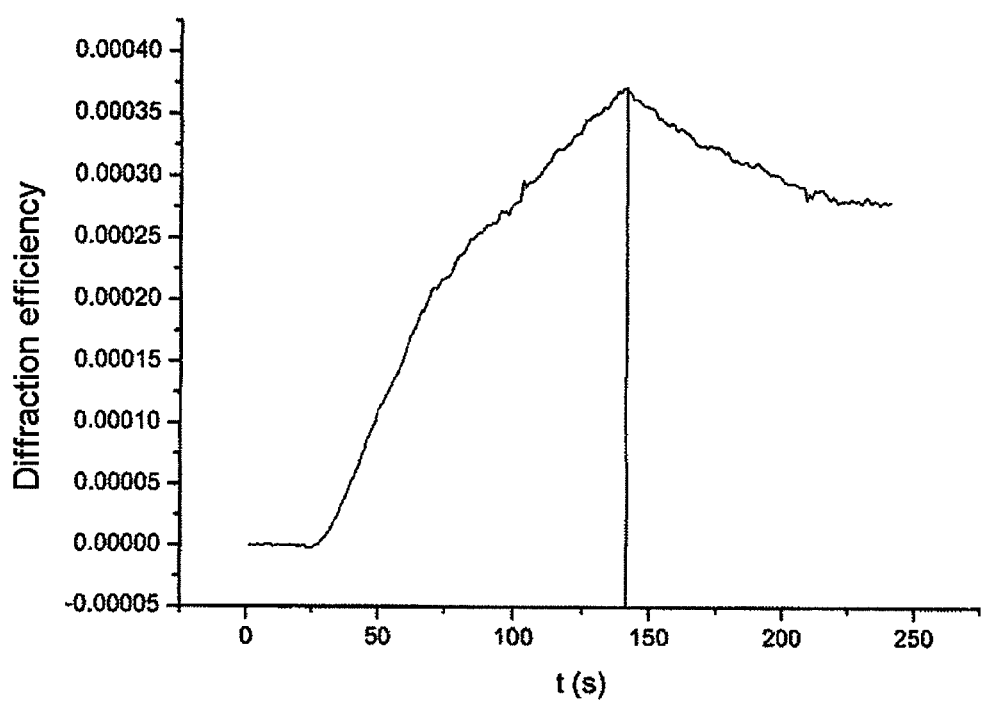
FIG. 5 plot of the diffraction efficiency at the first diffraction maximum of the hologram from example 3.
Figure 6:
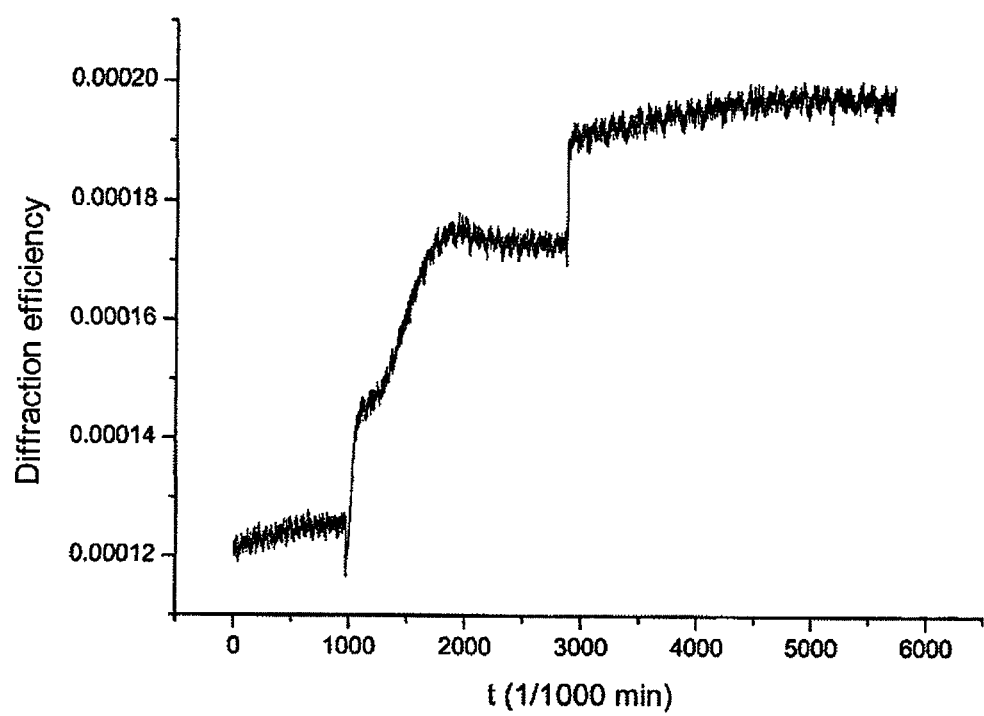
FIG. 6 plot of the diffraction efficiency at the first diffraction maximum of the hologram from example 4.

FIG. 5 plot of the diffraction efficiency at the first diffraction maximum for the hologram from example 3;

FIG. 6 plot of the diffraction efficiency at the first diffraction maximum for the hologram from example 4. Very weak diffraction was discernible, but it remained stable and was still discernible with the aid of a laser even after two days.

Numerous modifications and developments of the working examples described can be implemented.

Materials and Methods

The synthesis of the metal alkoxides was conducted in a darkened modified Stock high-vacuum apparatus with dried nitrogen as protective gas. The solvents used were dried and stored by standard methods. The titanium tetraisopropoxide used was distilled before use, the zirconium propoxide used was sublimed in a Kugelrohr still, and the photoinitiator used was dried over a molecular sieve.

The $^1$H and $^{13}$C NMR spectra were recorded on a Bruker AC 200 F NMR spectrometer in the solvents specified with 5-10 percent by volume of deuterochloroform $CDCl_3$. The CHN analysis was conducted by means of combustion analysis on a CHN-900 elemental analyzer from Leco Corporation.

Synthesis of $Ti(OC_3H_6COC_6H_5)_4$ (1)

2.73 g (9.58 mmol) of purified titanium tetraisopropoxide are initially charged at room temperature in 20 ml of anhydrous tetrahydrofuran. 6.16 ml (38.32 mmol) of 2-hydroxy-2-methyl-1-phenyl-1-propanone (Darocur 1173; Ciba Specialty Chemicals) in 20 ml of anhydrous tetrahydrofuran are slowly added dropwise to this solution. After stirring for 12 hours, the reaction solution is concentrated, in the course of which it turns dark orange. Still under reduced pressure, pale yellow crystals of $Ti(OC_3H_6COC_6H_5)_4$ (1) crystallize out of this solution over the course of 3 days. The supernatant solution is removed and the crystals are washed with tetrahydrofuran or recrystallized therefrom.

$^1$H NMR (THF; $CDCl_3$; ppm): 1.46 (s; 24H; $CH_3$), 8.16-8.20 (dd; 8H; aromatic H), 7.30-7.40 (m; 12H; aromatic H); $^{13}$C NMR (THF; $CDCl_3$; ppm): 26.76 (8C), 75.78 (4C), 126.67 (8C), 128.95 (8C), 130.87 (4C), 134.12 (4C), 202.41 (4C); elemental analysis: calculated: C, 68.59%; H, 6.28%. found: C, 68.69%; H, 6.07%.

The syntheses of $Zr(OC_3H_6COC_6H_5)_4$ (2) and $Ta(OC_3H_6COC_6H_5)_5$ (3) were conducted analogously.

Production of Coatings

The sols were prepared by dissolving the metal complexes in tetrahydrofuran or acetone and then mixing with a polyvinyl acetate solution (Synthomer M50) in THF or acetone.

To produce the films, several drops of the particular sols were applied to a glass microscope slide (Marienfeld), then aluminum film strips with a thickness of ~10-12 µm were placed on as spacers and the samples were covered with a further microscope slide. In addition, films were produced and examined without a second microscope slide.

The holography tests conducted by means of two-wave mixing with a model 2000 Ar+ ion laser (λ=351 nm), from *Spectra Physics*, and the writing process monitored in real-time transmission measurement with the aid of a helium laser (λ=632.9 nm) (see FIG. 1). The signal of the He laser was modulated by means of a chopper with a frequency of 124 Hz, and recorded by a detector connected to a lock-in amplifier (Stanford Research Systems SR 850 DSP).

Example 1

Exposure of 1

0.45 g of 1 in 4.00 g of a polyvinyl acetate solution (10 g of polyvinyl acetate, Synthomer M50, in 30 ml of THF). Exposure was effected 3× for 2 seconds each time (P=6.5 mW), and the hologram formed thereafter but was evident only with the aid of the He/Ne laser (FIG. 2).

Example 2

Exposure of 1 without Additional Microscope Slide as a Cover

A solution of 1 and a polyvinyl acetate solution (10 g for 30 ml of THF) in a ratio of 1:2 based on polyvinyl acetate were distributed on a microscope slide and left to dry. Where the layer was very thick it became whitish; otherwise it was clear. Thereafter, a hologram was recorded, with power 13.0 mW. Resting for 20 s was followed by exposure for 20 s, and then the course was monitored further for a further 80 s (FIGS. 3, 4).

The layer was applied with a coating knife. The wet film thickness was 120 µm. The diffraction efficiency of the layer produced with a coating knife was 1.4%.

Example 3

Exposure of 2 without Additional Microscope Slide as a Cover

A solution of 2 and a polyvinyl acetate solution (10 g for 30 ml of THF) in a ratio of 1:1 were distributed on a microscope slide and left to dry. In the course of this, the layer quite rapidly turned completely whitish. Nevertheless, it was possible to generate a hologram (power: 13.0 mW).

The hologram was first left to stand for 20 s and then exposed for 2 min; thereafter, the curve profile was monitored for 100 s (FIG. 5).

Example 4

Exposure of 3

7.73 g of 3 are mixed with polyvinyl acetate in a ratio of 1:1, and mixed with 25 ml of acetone. Undissolved 3 separates out of the white mixture. The supernatant clear solution is used to conduct holography experiments. The layer was left to stand for 1 min and then exposed for 3 min. Thereafter, the course of the diffraction efficiency at the first diffraction maximum was monitored for a further ~2.5 min (FIG. 6).

REFERENCE NUMERALS

10 Ar+ ion laser
12 He laser

14 Beam splitter
16 Mirror
18 Chopper
20 Sample
22 Detector connected to a lock-in amplifier

LIST OF LITERATURE CITED

U.S. Pat. No. 5,552,261
U.S. Pat. No. 5,529,473
US 2005/0101698 A1

The invention claimed is:

1. A process for producing an optical element, comprising:
 a) producing a composition comprising
  a1) at least one organic polymer;
  a2) at least one mono- or polynuclear metal complex of the formula:

$$X_{(m-n)}MR^1_n \qquad (I)$$

wherein M comprises Ti, Zr, Ta, V, Nb, Cr, Mo, W, Mn or Re;
   wherein $R^1$ comprises an α-hydroxy ketone, glyoxylate, or amino ketone;
   wherein X comprises a group without a light-sensitive group;
   wherein m corresponds to the valency of the metal; and
   wherein n is at least 1 to m;
   and
  a3) one or more solvents;
 b) applying the composition to a surface or to a mold; and
 c) generating a potential difference for directed diffusion of the at least one metal complex through local decomposition of the at least one metal complex by localized exposure to light, electrons or heat to cause a localized change in refractive index; and
  wherein the composition comprises 5 to 90% by weight of the at least one mono- or polynuclear metal complex.

2. The process as claimed in claim 1, wherein the at least one organic polymer is selected from the group consisting of poly(meth)acrylic acid and derivatives, poly(meth)acrylates, poly(meth)acrylonitriles, polystyrenes or polystyrene derivatives, polyalkenes, halogenated polyalkenes, polyvinyl acetate, polyvinylpyrrolidone, polyvinylcarbazole, poly(polyethylene glycol) (meth)acrylates, and poly(polyethylene glycol) di(meth)acrylates.

3. The process as claimed in claim 1, wherein $R^1$ comprises an α-hydroxy ketone.

4. The process as claimed in claim 1, wherein the at least one light-sensitive group does not act as a polymerization initiator.

5. The process as claimed in claim 1, wherein the potential difference comprises a chemical potential difference generated by exposure or electron irradiation.

6. The process as claimed in claim 5, wherein the chemical potential difference is generated by holographic or lithographic exposure techniques.

7. The process as claimed in claim 5, wherein the chemical potential difference is generated by a aligned mask exposure technique.

8. The process as claimed in claim 1, wherein the local decomposition forms metal oxides.

9. The process as claimed in claim 1, wherein the composition comprises 30 to 90% by weight of the at least one mono- or polynuclear complex.

10. A process for producing an optical element, comprising:
 a) producing a composition comprising
  a1) at least one organic polymer;
  a2) at least one mono- or polynuclear metal complex of the formula:

$$M\text{-}(-Z-CR^2R^3-CO-R^4)_m \qquad (II)$$

wherein M comprises Ti, Zr, Ta, V, Nb, Cr, Mo, W, Mn or Re;
   wherein Z comprises a heteroatom;
   wherein $R^2$ and $R^3$ are the same or different and comprise a $C_1$-$C_{12}$ alkyl radical or an aryl radical;
   wherein $R^4$ comprises a $C_1$-$C_6$ alkyl group or an aryl group which is unsubstituted or substituted by $C_1$ to $C_3$ alkyl radicals, and the groups may optionally contain heteroatoms or halogens; and
   wherein m corresponds to the valency of the metal;
  a3) one or more solvents;
 b) applying the composition to a surface or to a mold; and
 c) generating a potential difference for directed diffusion of the at least one metal complex through local decomposition of the at least one metal complex by localized exposure to light, electrons or heat to cause a localized change in refractive index; and
  wherein the composition comprises 5 to 90% by weight of the at least one mono- or polynuclear metal complex.

11. A process for producing an optical element, comprising:
 a) producing a composition comprising
  a1) at least one organic polymer;
  a2) at least one mono- or polynuclear metal complex which comprises at least one light-sensitive group selected from the group consisting of alkyl benzoylformates, amino ketones, benzoin ethers, dimethyl ketals, glyoxylates, hydroxy ketones, hydroxyphenones, metallocenes, phenylpropanes, and phosphine oxides; and which comprises Ti, Zr, Ta, V, Nb, Cr, Mo, W, Mn or Re; and
  a3) one or more solvents;
 b) applying the composition to a surface or to a mold; and
 c) generating a potential difference for directed diffusion of the at least one metal complex through local decomposition of the at least one metal complex by localized exposure to light, electrons or heat to cause a localized change in refractive index; and
  wherein the at least one organic polymer does not have any reactive groups that polymerize or polycondense as a result of decomposition of the at least one mono- or polynuclear metal complex and the composition does not comprise any monomers; and
  wherein the composition comprises 5 to 90% by weight of the at least one mono- or polynuclear metal complex.

12. The process as claimed in claim 10, wherein the composition comprises 30 to 90% by weight of the at least one mono- or polynuclear complex.

13. The process as claimed in claim 11, wherein the composition comprises 30 to 90% by weight of the at least one mono- or polynuclear complex.

* * * * *

UNITED STATES PATENT AND TRADEMARK OFFICE
CERTIFICATE OF CORRECTION

PATENT NO. : 9,052,588 B2  
APPLICATION NO. : 13/124850  
DATED : June 9, 2015  
INVENTOR(S) : de Oliveira et al.

Page 1 of 1

It is certified that error appears in the above-identified patent and that said Letters Patent is hereby corrected as shown below:

On the Title page, Item (73), Assignee:

Change "Leibniz-Institut fuer Neue Marterialien gemeinnuetzige GmbH, Saarbruecken (DE)"

to

--Leibniz-Institut fuer Neue Materialien gemeinnuetzige GmbH, Saarbruecken (DE)--

Signed and Sealed this
Sixth Day of October, 2015

Michelle K. Lee
*Director of the United States Patent and Trademark Office*